US008705819B2

(12) United States Patent
Carlsen et al.

(10) Patent No.: US 8,705,819 B2
(45) Date of Patent: Apr. 22, 2014

(54) ADJUSTING ACQUISITION PROTOCOLS FOR DYNAMIC MEDICAL IMAGING USING DYNAMIC MODELS

(75) Inventors: Ingwer Curt Carlsen, Hamburg (DE); Daniel Bystrov, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 833 days.

(21) Appl. No.: 12/665,441

(22) PCT Filed: Jun. 19, 2008

(86) PCT No.: PCT/IB2008/052424
§ 371 (c)(1),
(2), (4) Date: Dec. 18, 2009

(87) PCT Pub. No.: WO2008/155738
PCT Pub. Date: Dec. 24, 2008

(65) Prior Publication Data
US 2010/0183206 A1 Jul. 22, 2010

(30) Foreign Application Priority Data
Jun. 21, 2007 (EP) .................................. 07110774

(51) Int. Cl.
*G06K 9/00* (2006.01)
(52) U.S. Cl.
USPC ........................................................ 382/128
(58) Field of Classification Search
USPC ...................... 382/128, 131; 378/8
See application file for complete search history.

(56) References Cited

U.S. PATENT DOCUMENTS

| 5,583,902 | A  | * | 12/1996 | Bae ..................................... 378/8 |
| 5,687,208 | A  | * | 11/1997 | Bae et al. .......................... 378/8 |
| 6,195,409 | B1 | * | 2/2001  | Chang et al. .................... 378/20 |
| 6,236,706 | B1 | * | 5/2001  | Hsieh ................................ 378/8 |
| 6,782,071 | B1 | * | 8/2004  | Tsuyuki ............................ 378/4 |
| 6,850,585 | B2 |   | 2/2005  | Hsieh et al. |
| 8,428,690 | B2 | * | 4/2013  | Li et al. ......................... 600/424 |

(Continued)

FOREIGN PATENT DOCUMENTS

| WO | 0057361 A1    | 9/2000 |
| WO | 2004080309 A2 | 9/2004 |

OTHER PUBLICATIONS

Pan, T., et al.; 4D-CT imaging of a volume influenced by respiratory motion on multi-slice CT; 2004; Med. Phys.; 31(2)333-340.

(Continued)

*Primary Examiner* — Irakli Kiknadze

(57) ABSTRACT

The invention relates to automatically adjusting an acquisition protocol for dynamic medical imaging, such as dynamic CT, MRI or PET imaging. The protocols are adjusted based on anatomic and dynamic models (10, 12, 14) which are individualized or fitted to each patient based on a scout scan (6, 8). The adjustment can compensate for changes in the patient due to patient motion (e.g. breathing or heartbeat) or flow of contrast or tracing agent during the sequence. This ensures that changes in the reconstructed images are indicative of pathological changes in the patient and not caused by patient motion or changes in scanning parameters or timing. The dynamic model can be a motion model (12) used to predict the motion of anatomic/physiologic features, typically organs, during scanning, or a haemodynamic model (14) used to predict flow of the contrast agent allowing for precise timing of the scanning sequence.

10 Claims, 2 Drawing Sheets

(56) References Cited

U.S. PATENT DOCUMENTS

| | | | |
|---|---|---|---|
| 2002/0010551 A1 | 1/2002 | Wang et al. | |
| 2003/0108149 A1* | 6/2003 | Tsuyuki | 378/54 |
| 2003/0161435 A1* | 8/2003 | Ozaki | 378/4 |
| 2003/0161436 A1* | 8/2003 | Boyd et al. | 378/8 |
| 2003/0187358 A1* | 10/2003 | Okerlund et al. | 600/443 |
| 2004/0008819 A1* | 1/2004 | Drummond et al. | 378/162 |
| 2004/0127789 A1* | 7/2004 | Ogawa | 600/425 |
| 2005/0154292 A1 | 7/2005 | Tank | |
| 2005/0267348 A1 | 12/2005 | Wollenweber et al. | |
| 2006/0050840 A1* | 3/2006 | Ikeda et al. | 378/8 |
| 2006/0178836 A1* | 8/2006 | Bai et al. | 702/19 |
| 2006/0233296 A1* | 10/2006 | Wakai et al. | 378/8 |
| 2007/0066892 A1* | 3/2007 | Haras et al. | 600/425 |
| 2007/0121780 A1* | 5/2007 | Watanabe | 378/8 |
| 2008/0192887 A1* | 8/2008 | Weese et al. | 378/41 |
| 2008/0240337 A1* | 10/2008 | Galant et al. | 378/4 |
| 2009/0129536 A1* | 5/2009 | Ichihara et al. | 378/4 |
| 2009/0202121 A1* | 8/2009 | Fenchel et al. | 382/128 |
| 2009/0208079 A1* | 8/2009 | Vaillant et al. | 382/131 |

OTHER PUBLICATIONS

Qiao, F., et al.; Compensating Respiratory Motion in PET Image Reconstruction Using 4D PET/CT; 2005; IEEE Nuclear Science Symposium Conf. Record; 5:2595-2598.

Farncombe, T. H., et al.; Investigating Acquisition Protocols for Gated, Dynamic Myocardial Imaging in PET and SPECT; 2003; IEEE Nuclear Science Symposium and Medical Imaging Conf.; 5:3272-3275.

Vembar, M., et al.; A dynamic approach to identifying desired physiological phases for cardiac imaging using multislice spiral CT; 2003; Med. Phys.; 30(7)1683-1693.

* cited by examiner

ADJUSTING ACQUISITION PROTOCOLS FOR DYNAMIC MEDICAL IMAGING USING DYNAMIC MODELS

FIELD OF THE INVENTION

The present invention relates to dynamic medical imaging, that is to say the acquisition of a plurality images over a period of time. In particular, the invention relates to adjusting an acquisition protocol for dynamic medical imaging.

BACKGROUND OF THE INVENTION

Medical imaging is a technology that has evolved substantially over the past few decades with an increasing diversity of modalities—Magnetic Resonance Imaging (MRI), Computed Tomography (CT), Nuclear Medicine (NM) and Positron Emission Tomography (PET), to name but a few. Although the traditional notion of medical imaging involves the acquisition of a "static" image that captures the anatomy of an organ/region of the body, increasingly the use of more sophisticated imaging techniques allows dynamic studies to be made which provide a temporal sequence of images which may characterize physiological or pathophysiological information.

Dynamic medical imaging may involve the use of an imaging or contrast agent to increase selectively the contrast of a region in the image or to follow the uptake or flow in a region, so called bolus tracking. For example, one may inject into a patient a compound which has a biophysical, molecular, genetic or cellular affinity for a particular organ, disease, state or physiological process. Such contrast agents are selected to have a property that provides enhanced information to a given imaging modality by altering imaging conditions (normally by altering the contrast) to reflect the behavior of the compound in the body. The contrast agent will thereby move or change its distribution during dynamic medical imaging, and the optimal setting for the image acquisition will vary for consecutive acquisitions.

Also, dynamic medical imaging may require a patient to spend considerable time in an imaging device in order to acquire an image sequence. During this time, a patient may move due to natural bodily motion such as respiration, heartbeat, etc. This motion may corrupt the accuracy of the resulting images.

Furthermore, dynamic follow-up studies have to be done to monitor e.g. the changes of a pathology to determine its exact nature or its response to therapy. These follow-up studies may be taken days or weeks apart and require independent patient positioning. Changes in patient position and status between the follow-up studies may adversely affect the quality of the resulting images.

WO 04/080309 describes a device and method for adapting recording parameters in CT scanning using a pilot scan and static patient model. For imaging where dynamics is involved, the prior art provide techniques for motion correction after acquisition, see for example WO 00/57361. Such techniques do no provide means for improving the acquisition process of the dynamic imaging, only for correcting the acquired images.

SUMMARY OF THE INVENTION

It is therefore a problem that dynamic imaging sequences often need to be redone since the reconstructed images cannot be used due to wrong timing in relation to organ motion or contrast agent flow.

Hence, an improved scheme for compensating for motion during or between dynamic medical imaging would be advantageous, and in particular a more efficient and/or reliable way of adjusting an acquisition protocol for dynamic medical imaging would be advantageous.

Most of the current imaging protocols stem from the old days of single image acquisition on slow low-resolution scanners. These acquisition protocols provide only crude pre-settings and have to be manually adjusted to individual patient settings and motion. Depending on the experience and skills of the technician, this may result in sub-optimal settings leading to sub-optimal image quality, i.e. inefficient dose usage or even higher X-ray exposure in case the study has to be redone.

Accordingly, the invention preferably seeks to mitigate, alleviate or eliminate one or more of the above mentioned disadvantages singly or in any combination. In particular, it may be seen as an object of the present invention to provide adjusted acquisition protocols facilitating more standardized, better quantifiable, more reproducible and simplified dynamic medical imaging.

In a first aspect of the invention, it provides a method for adjusting an acquisition protocol for dynamic medical imaging of a body volume of a patient, the method comprising:
providing a reconstructed image of the body volume of the patient;
providing an anatomic model of the body volume and fitting the model to the body volume using the reconstructed image;
providing a preliminary acquisition protocol for dynamic medical imaging of the body volume;
providing a dynamic model for temporal variations in one or more anatomic and/or physiologic features in the anatomic model;
using the dynamic model to adjust the provided preliminary acquisition protocol to compensate for the temporal variations in said one or more features during dynamic medical image acquisition of the body volume.

In a second aspect, the invention provides a computer program product for adjusting a preliminary acquisition protocol for dynamic medical imaging of a body volume of a patient in accordance with claim 7.

In a third aspect, the invention provides a computer program product for updating a medical imaging apparatus to apply dynamic models in adjusting a preliminary acquisition protocol for dynamic medical imaging of a body volume of a patient, the product comprising means for installing software applications which, based on data representing a dynamic model for temporal variations in one or more features in an anatomic model,
provides the following when executed by a processor:
using the dynamic model to adjust the provided preliminary acquisition protocol to compensate for the temporal variations in said one or more features during dynamic medical image acquisition of the body volume.

The computer program product may for example be an update for download and installation over a network.

In a fourth aspect, the invention provides a medical imaging apparatus comprising a unit for adjusting an acquisition protocol for a dynamic imaging sequence, the apparatus further comprising:
instructions for performing a scout scan of a body volume to be imaged;
a preliminary acquisition protocol for dynamic medical imaging of the body volume;
wherein the unit has access to data representing an anatomic model of the body volume and to a data representing a dynamic model for temporal variations in one or more features in the anatomic model, and wherein the unit comprises:

means for fitting the anatomic model to the body volume based on reconstructed image data from the scout scan;

means for, on the basis of the anatomic and dynamic models, adjusting the preliminary acquisition protocol to compensate for the temporal variations in said one or more features during dynamic medical image acquisition of the body volume.

In the following, a number of preferred and/or optional features and elements will be described in relation to various embodiments of the invention. Features or elements described in relation to one embodiment or aspect may be combined with or applied to the other embodiments or aspects where applicable.

An acquisition protocol may be a set of parameters, apparatus settings and operation instructions used in performing a dynamic imaging sequence. Typical examples of such will be provided in relation to the detailed description of the invention. An acquisition protocol may be related to a predetermined clinical application, and the dynamic models may be selected among several possible to suit the predetermined clinical application. The adjustment of the acquisition protocol thereby means altering of, or possibly adding, parameters, apparatus settings and operation instructions of the protocol. The adjustments are preferably carried out on the basis of previously used acquisition protocols, previously acquired images or additional non-image sensor information of the patient. It thereby follows that the broadest aspects of the invention does not relate to the recording or interpretation of a clinical picture, but merely to the preparatory steps for performing a dynamic imaging sequence. Also, none of the steps of the adjusting of the acquisition protocol involves interaction with the body of the patient.

The anatomic model is used to predict the mean location and shape of the anatomic and/or physiologic features of interest. An anatomic and/or physiologic feature is typically an organ, but may also refer to any other feature such as a specific joint, muscle, blood vessel or to a position inside the patient at which the pathology of interest is located.

The motion model is used to predict the motion of the anatomic and/or physiologic features during the scanning sequence, and i.e. to predict the location and shape at a given point in time. Similarly, the haemodynamic model is used to predict the expected timing of the contrast agent at the anatomic and/or physiologic features of interest. The term dynamic model is used to designate the motion model and/or the haemodynamic model. Using the dynamic models to compensate for the temporal variations in anatomic and/or physiologic features means that parameters, apparatus settings or operation instructions are altered so that consistency in the image acquisition in relation to movements is achieved. An example may e.g. timing of the image acquisition with patient breathing pattern or with the propagation of contrast agent in the blood vessels of the patient.

Individualizing of the various models or of the acquisition protocol means that the model is adapted or the protocol is adjusted to fit a specific patient, e.g. by altering details in the models or the protocol to the patient's size, position, breathing, heartbeat, contrast agent injection scenario etc.

The initially provided reconstructed image of the body volume may be from a scout scan performed in connection with the imaging sequence or from a previous scanning of the patient. This initially provided image of the body volume is used for individualizing the various models, and need not have the same resolution or quality as the images from the scanning sequence.

If the initially provided image of the body volume is from a scout CT or X-ray scan, the scout scan may preferably be performed using a reduced recording resolution and/or a lower X-ray dosage than prescribed by the preliminary acquisition protocol. This provides the advantage of exposing the patient to lower X-ray dosage as well as increasing the patient throughput since a lower quality/resolution image is generally acquired faster. Similar considerations apply to PET imaging.

Similarly, if the initially provided image of the body volume is from e.g. a scout MRI scan, the lower resolution requirements may allow for a faster and easier image acquisition. Initially provided MRI images, from scout scans or elsewhere, may be of lower spatial resolution, equivalent to scanning only a centre portion of the k-space.

In the alternative, the initially provided image is provided by retrieving a previously stored reconstructed image of the body volume of the patient, either from a previous scout scan or from a previous scanning sequence. For this purpose, the apparatus may comprise a repository for holding previously recorded reconstructed images from the patient. This may be advantageous when several scanning sequences are performed in a row as long as the patient is not repositioned, e.g. during a multi-tracer study. Here, one need not take a new scout scan for use in individualizing the various models every time a sequence is initiated. Instead, a reconstructed image from a previous scout scan or scanning sequence may be used.

The preliminary acquisition protocol may be a standardized acquisition protocol for the relevant clinical application, or it may be a previously adjusted acquisition protocol for the patient retrieved from a repository. For this purpose, the apparatus may comprise a repository for holding previously acquisition protocols and means for retrieving preliminary acquisition protocols from the repository and for storing adjusted acquisition protocols for a patient in the repository. Thus, an adjusted acquisition protocol may be subject to further adjustments both during the imaging sequence or between individual sequences based on feedback from analysis of previous images in the sequence.

The second and third aspect of the invention relates to a computer program product. Such computer program product is adapted to enable a computer system comprising at least one computer having data storage means associated therewith to control a medical imaging apparatus or a unit of such carry out the invention. These aspects of the invention are particularly, but not exclusively, advantageous in that the present invention may be implemented by a computer program product enabling a computer system to perform the operations of the first aspect of the invention. Thus, it is contemplated that some known medical imaging apparatus, or a unit of such, may be changed to operate according to the present invention by installing a computer program product on a computer system controlling the said optical recording apparatus. Such a computer program product may be provided on any kind of computer readable medium, e.g. magnetically or optically based medium, or through a computer based network, e.g. the Internet.

The invention overcomes the limitations of conventional dynamic medical imaging acquisition protocols. When it comes to accurate bolus tracking or imaging of the uptake of the contrast agent in a tumor or a target organ, the fast acquisition rates supported by the latest generation scanners require a far more accurate timing than conventional imaging. In addition, to fully exploit the better resolution requires more accurate motion compensation over the target field-of-view, i.e. more accurate gating/triggering according to breathing or heart motion. The more accurate imaging capabilities become, the higher the demand for patient-specific optimization of the acquisition control. The invention aims at providing an automatic procedure, as well as an apparatus or unit and computer program products implementing this procedure, for adjusting protocol settings of dynamic image acquisition to fully exploit the capabilities of current and future dynamic medical imaging scanners. In addition, it is desired that the various embodiments of the invention provides at least one or more of the following advantages:

provide adaptive, fault tolerant protocols that greatly simplify scanner operation
to make the acquisition protocols fault tolerant to ensure imaging according to diagnostic quality standards
to make high-speed dynamic imaging less sensible to changes in the timing of the acquisition protocol
to avoid duplicate imaging for economical reasons
to speed up and simplify the preparation of the acquisition for higher patient throughput and better patient comfort
achieve comparable and reproducible images
to improve comparability to follow-up scans for better sensitivity to morphological changes of lesion to monitor for example tumor growth over time or tumor response to treatment, etc.
make more efficient use of X-ray dose, i.e. providing better image quality for the same X-ray dose or providing the same image quality for less X-ray dose.

The basic idea of the invention is to, automatically and based on dynamic models, adjust the acquisition protocols to take into account changes in the patient due to motion or tracing agent flow so that changes in the reconstructed images are indicative of pathological changes in the patient and not caused by patient motion or changes in scanning parameters or timing.

These and other aspects of the invention will be apparent from and elucidated with reference to the embodiments described hereinafter.

BRIEF DESCRIPTION OF THE DRAWINGS

The present invention will now be explained, by way of example only, with reference to the accompanying Figures, where.

DETAILED DESCRIPTION OF THE PREFERRED EMBODIMENTS

Figure 1:
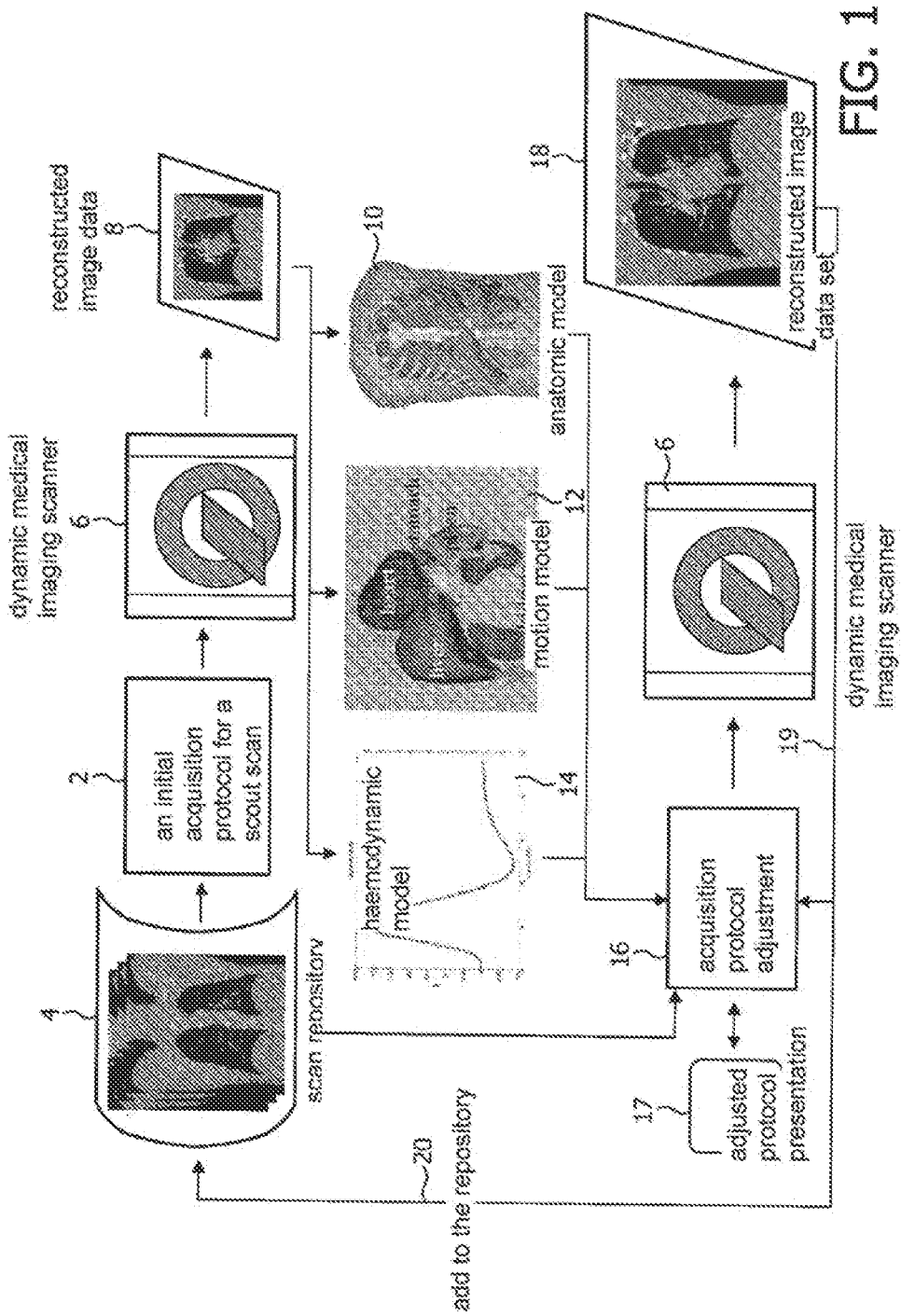
FIG. 1 is a flow-chart for a method or computer program products according to embodiments of the invention.

Embodiments of the invention relating to the method, computer program products and software updating packages, as well as usage of the embodiment relating to an apparatus or unit, for adjustment of an acquisition protocol on the basis of anatomic and dynamic models are described in relation to the flow chart of FIG. 1. The description is outlined in relation to the method, but are equally applicable to the individual operations carried out by software or steps carried out when using the apparatus or unit.

Prior to initiating dynamic medical imaging, a clinical application of the resulting images has typically been determined, e.g. examination, confirmation of a preliminary diagnose, monitoring progress of a treatment or development in a disease. The clinical application, or the purpose of the imaging, determines which body volume and which organs or anatomic/physiologic features are to be imaged and by which imaging method. The embodiments of the invention can be applied to a wide variety of clinical application and imaging methods.

In Box 2, an initial acquisition protocol is provided for a scout scan. In case the patient has been scanned before, an acquisition protocol from previous scans of the patient is retrieved from a repository 4. In case the patient is scanned for the first time, a conventional "standard" acquisition protocol for the relevant clinical application and imaging method is used.

The scan repository 4 accumulates and relates the scan protocols that a patient has been subjected to, and preferably also the corresponding image data. It is the core of the individualization or 'learning' capabilities of the apparatus or unit to adapt to changes of the patient, the disease or the imaging requirements by the operator, typically a radiologist or a technician.

A scout scan of the body volume is acquired by the dynamic medical imaging scanner 6, typically but not limited to a MRI-, CT-, or PET-scanner. Scout scan image data 8 of the body volume is reconstructed.

An anatomic model 10 of the body volume is provided and individualized to the reconstructed image data 8 from the scout scan, typically by fitting or registering the model to the reconstructed image data 8, e.g. by scaling or mathematically transforming such as by non-linear elastic deformation. The purpose is to adjust the physical dimensions of the anatomic model to the patient, so that the anatomic model can be used to predict positions and dimensions of organs and anatomic/physiologic features in the field-of-view of the body volume. This information is useful for optimizing e.g. dose distribution and reconstruction parameters.

Whereas the anatomic model is individualized with respect to the static parameters of the patient anatomy, the invention also applies a dynamic model for temporal variations in one or more features in the body volume or anatomic model. Depending of the clinical application and imaging method, the model can be a motion model 12 and/or a haemodynamic model 14. The motion model 12 is by construction aligned with the anatomy model. It is used to predict the motion patterns due to patient motion with respect to previous scans and expected organ motion during the scan. This information is essential to adjust acquisition parameters such as table speed, gating and triggering levels etc. to minimize the effect of patient and/or organ motion. The haemodynamic model 14 is used in imaging methods for more accurately tracking of an injected contrast agent. It is by construction aligned with the anatomy model, and provides information to predict the flow of the contrast agent into the target organ. This information is essential for more accurate timing of dynamic studies to exploit the better resolution and higher acquisition speed of advanced scanner for more accurate targeting and tracking the contrast agent.

In Box 16, an acquisition protocol is adjusted using the information from the anatomic and dynamic models. Again, an acquisition protocol from repository 4 is used as the basis of the adjustment if the patient has been scanned previously, if not, a standard acquisition protocol for the relevant clinical application and imaging method is used as the basis of the adjustment.

Box 17 illustrates the optional step of presenting the adjusted protocol to an operator, typically a radiologist or technician, for final adjustments and approval. Thereafter, the adjusted protocol is applied in scanner 6 for the eventual acquisition scans resulting eventually in a reconstructed image data set 18 from the imaging sequence.

As an optional further step illustrated by connector 19, the eventually reconstructed image data set 18 is evaluated by the operator, and the acquisition protocol is adjusted for the next image acquisition for the current dynamic study if necessary.

Also, as illustrated by connector 20, the eventually reconstructed image data set 18 together with the acknowledged protocol are added to the repository 4 to define a better initial scan protocol for the next exam of this patient. This feature contributes to the individualization or 'learning' capabilities of the apparatus or unit.

When implemented as computer program products, the boxes and steps described in relation to FIG. 1 in the above can be implemented as operations carried out by one or more software applications. The computer program product for updating a medical imaging apparatus to apply the method comprises only software applications for carrying out the operations which the apparatus can not already perform. Thus, the extent of such updating software may depend on the specific model of the medical imaging apparatus and any previously installed software updates.

In the following, examples of parameters in an acquisition protocol and how they are changed by the adjustment of the protocol in accordance with the invention will be described.

Examples of typical acquisition protocol parameters, how they are typically determined in present scanning procedures, and how they are adjusted in an embodiment of the invention will be given in the following.

One parameter can be the total amount of contrast agent used in bolus tracking. This is typically determined by the patient weight datasheet. As an example of an adjustment, the distance between point of injection and target region can be determined by the anatomic model and the dispersion of the bolus can be predicted by the haemodynamic model. This may allow for a more correct dosage of contrast agent, providing better image quality and the of less contrast agent (which may be expensive and which may be hazardous for the patient).

Another parameter can be the timing of the start of scanning sequence, e.g. the delay after injection of contrast agent or synchronization with patient motion. This is typically based on the operator's experience. As an example of an adjustment, the haemodynamic model can be used to automatically time scan initiation with contrast agent injection, and the motion model can be used to for automatically timing with breathing/heartbeat based on motion sensor input.

Thus, from one point of view, the experience of the operator and the guidelines to be followed by the operator to determine acquisition protocol parameters are, according to some embodiments of the invention, augmented by the anatomic and dynamic models, thereby allowing automatic optimization of the acquisition protocol.

In the following, some examples of the anatomic and dynamic models used by the invention are given. It is noted that these are present examples of such models, and that this is an area of active research. Hence, future models performing a similar function but having a different format may be developed, the use of which are considered to fall within the scope of the present invention.

The anatomic model 10 may be a surface model in which a data representation of a three-dimensional wire-frame or mesh (typically consisting of triangles) outlines surfaces of anatomic/physiologic features in the patient, typically organs. Alternatively, the anatomic model 10 may be a volume model consisting of a grid of volume elements (referred to as voxels), wherein each voxel is designated as lying within, or primarily within, a particular organ. In another alternative, the anatomic model 10 may be a parametric model with parametric equations describing the position of organ surfaces. Each of these models can be individually adjusted (e.g. by scaling or non-linear elastic deformation) to the image data of the scout scan, in order to fit the organ positions and sizes of the model to those of the patient in his/her present position.

The motion model 12 is used to predict the motion of the organs or other anatomic/physiologic features of the patient, motion cased by e.g. breathing motion; heartbeat, peristaltic motions, change in position of the patient; filling ratio of bladder, stomach and bowel, etc. The motion model does not only relate to motions during an imaging sequence (seconds-hours), but also to motion between subsequent imaging sequences (hours-days). Motion models may be integrated with the different anatomic models described in the above, by including a time-parameter. For the surface and volume models, each surface or volume element may be associated with a motion vector describing the movement of that particular element. A general motion vector field can be used which describes the standard motion of the anatomic entities for the typical patient, or the motion model may be individually adapted to use motion vectors derived for the particular patient. For the parametric anatomic model, the motion can be integrated by incorporation of an extra parametric variable, namely time or sensor signals monitoring the breathing status or the heart beat. Such parametric models may be motion fields represented by mathematical transformations, e.g. represented as one of the various forms of spline transformations.

In order to individually adapt a motion model, the motion for the patient can be monitored, typically by use of one of the following scenarios:

Sensors: breathing can be estimated by belt around chest, heartbeat by ECG, which data can be fed to the motion model so that it can be individually adapted.

Scan itself: Dynamic imaging scans are typically carried out over a period of time; during breath-hold or in timing with breathing or ECG, so that the motion pattern can be determined from the scan itself and fed to the model for subsequent adaptation.

As is evident from the above, anatomic and motion models, 10 and 12, can reside in the same computer representation, e.g. by annotating each surface or volume element with a motion vector or by including a time or sensorparameter in a parametric model.

The function of the haemodynamic model 14 is to predict when the contrast agent arrives where in the blood system, so that the image acquisition or scan sequence can be automatically started or timed with the intravenous injection of contrast agent or another tracing substance: Typical desired properties of contrast or tracing agents in different fields are increased X-ray attenuation for CT/X-ray, altered paramagnetic properties for MRI, and incorporation of a radioisotope for nuclear medicine/PET.

The haemodynamic model 14 can be a time curve, an equation, or a time-annotated anatomic model of the vasculature of interest describing when and at which amount the contrast agent passing through a given blood vessel cross section as a function of time. In one embodiment the operator should feed or select the point of injection and the target region, whereby the individually adapted anatomic model 10 can predict the relevant distances needed for individual adaptation of the haemodynamic model 14. In one embodiment, the timing is carried out by e.g. monitoring the aorta, and when contrast agent is detected in the aorta, a marker is set and the individually adapted haemodynamic model is used to predict arrival in the target region. Haemodynamic models are currently a topic of active research, and future models performing similar functions are considered to fall within the scope of the present invention.

Referring again to FIG. 1, the overall execution of the method or software, or operation of the apparatus or unit, for adjusting the parameters that constitute the acquisition protocol on the basis of models 10, 12 and 14 can be summarized as:

- aligning anatomic model 10 with size and shape of patient from scout scan image data 8;
- determining status of the organ motion, e.g. by sensors or dynamic scanning, and correlate with motion model 10 to predict motion;
- monitor contrast agent injection or flow, and use haemodynamic model 14 to time imaging sequence with the agents passing through the target region.

In the following, details of the invention are illustrated in relation to the specific clinical application example of contrast enhanced liver imaging. The liver varies in size and shape, its position is affected by breathing motion, and optimal contrast in arterial, portal venous, and late phases depends on the circulatory connection of the liver. Accordingly, optimal contrast in the various phases depends on the amount of contrast agent, the injection rate, the injection timing and the scan delays for imaging the different phases. Currently, it requires a skilled operator to heuristically determine the optimal acquisition settings taking into account the patient size, weight, and constitution as well as any circulatory disturbances.

For this application, an embodiment of the method or software according to the invention could be implemented as follows, referring to FIG. 1:

The repository 1 provides any previous scan protocols of the patient that result from previous exams and incorporate any previous adjustments to the individual status of the patient.

The anatomic model 10 consists of a surface model describing the body surface, the organs and the blood vessels. Using active surface techniques, this model can be aligned with the geometric proportions determined from the image data 8 from the low-dose 3D scout scan. This determines the field-of-view to be covered for this study.

A motion model 12 in form of a three-dimensional vector field is by construction aligned with the anatomic model 10 and relates the expected shifts of the liver position with the breathing cycle. This information provides the parameters for motion-compensated acquisition and reconstruction techniques of the individual phase images.

The haemodynamic model 14 is by construction aligned with the anatomic model 10 and relates the amount of injected contrast agent and the injection rates with the contrast expected in the liver over time. This determines the amount of contrast agent to be injected and defines optimal the injection timing and rate as well as the corresponding timing of the acquisition of the different phase images.

After each phase, the protocol for the acquisition of the next phase is adjusted according to the status of the contrast study and the result of the previous phase. Any deviation of the predicted Hounsfield value from the actually observed one is used to re-adjust the models and related acquisition parameters.

The protocol for the next phase acquisition is displayed to the technician/radiologist for approval or interactive correction.

The repository 1 is augmented by the finally executed protocol and the cycle starts anew until the acquisition is gone through all phases required.

The invention may be applied in relation to any dynamic CT imaging, where it has the advantage of providing simplified operation and better support of diagnosis and therapy. Also, the apparatus or unit may be used to adjust acquisition protocols for other dynamic medical imaging techniques such as MRI or PET scanning Other potential applications may e.g. be to improve quality and comparability dynamic MR imaging involving the administration and tracking of MR-visible contrast agents such as perfusion or angiographic studies, as well as PET studies to characterize tumor physiology for improved diagnosis and therapy response assessment.

As described previously, the invention can be implemented in any suitable form including hardware, software, software packages for updating, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Figure 2:
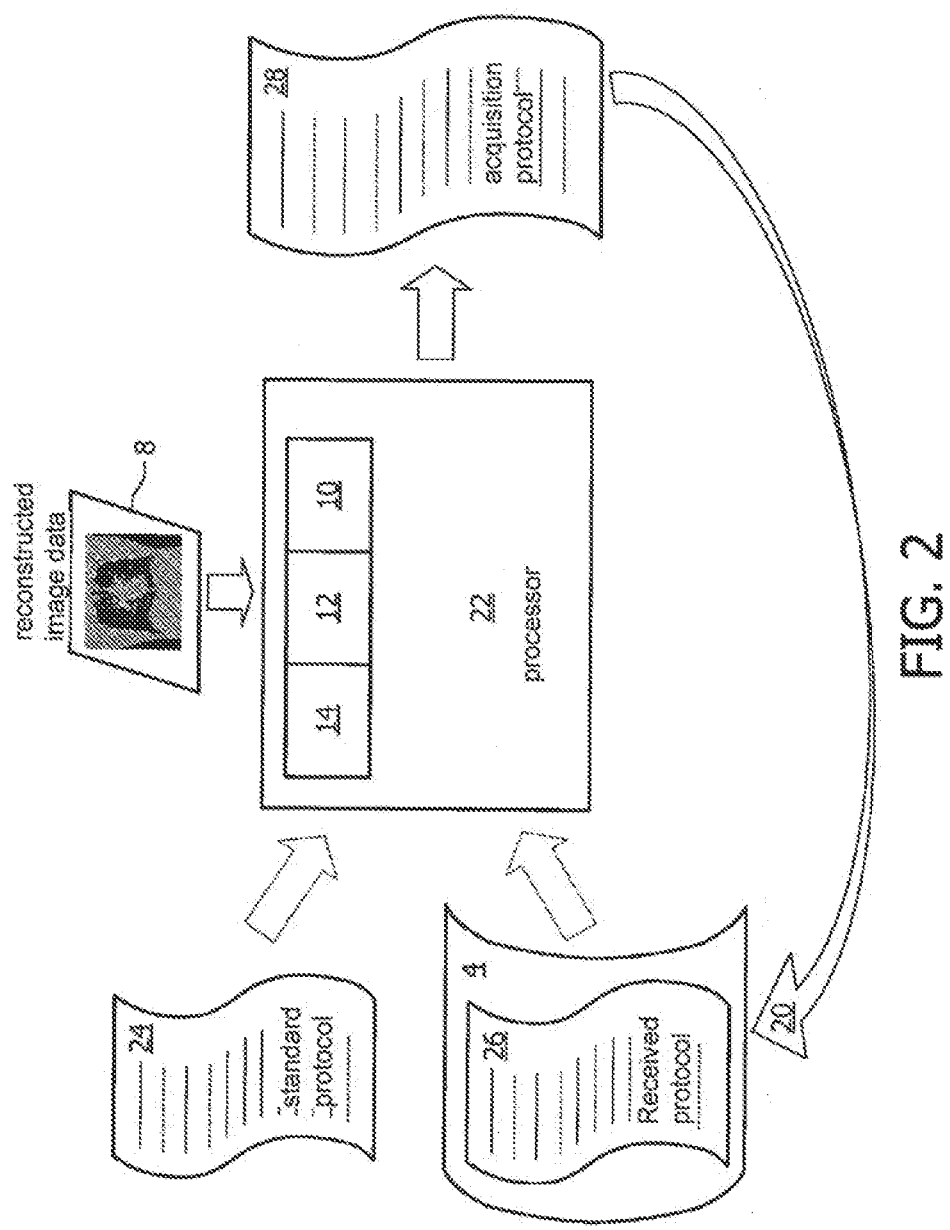
FIG. 2 illustrates a unit in a medical imaging apparatus, for adjusting acquisition protocols in accordance with an embodiment of the invention.

FIG. 2 illustrates a data processor 22, such as a computer, embodying the embodiment relating to an apparatus or unit, e.g. for executing computer program products according to other embodiments of the inventions. The illustration of FIG. 2 should be understood in the light of the flowchart described in relation to FIG. 1.

In FIG. 2, the data processor 22 receives an acquisition protocol whose parameters are to be adjusted. The protocol may be a standard protocol 24 if no previously adjusted protocol exists for the patient, or may be a previously adjusted protocol 25 from previous examinations of the patient stored in the repository 4. Having received a protocol (24 or 26), the data processor 22 either executes software or carries out instructions from other software or an operator, to perform the adjustment of the received protocol on the basis of anatomic and dynamic models (10, 12, 14) as described in relation to FIG. 1. The data processor 22 has access to the various models, either by holding a data representation in internal storage as shown or by accessing them on an external storage. Also, the data processor 22 receives image data 8 resulting from the scout scan for use in the individual adaptation of the models 10, 12 and 14.

The data processor 22 outputs an adjusted acquisition protocol 28 for use in the dynamic imaging of the patient under examination. and may also facilitate storing of the adjusted acquisition protocol 28 in the repository 4, as illustrated by arrow 20.

The data processor 22 may form the entirety or a part of an apparatus or unit for carrying out the invention. Hence, the data processor 22 may be part of a scanner, such as a CT, MRI or a PET scanner, thereby allowing the scanner to operate in accordance with the basic idea of the invention.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A method for dynamic medical imaging of a body volume, the method comprising acts of:
   fitting organ positions and sizes of an anatomic model of the body volume to a reconstructed image of the body volume;
   imaging the body volume using acquisition protocol initially comprising a preliminary acquisition protocol; and
   during the imaging,
      adjusting the acquisition protocol to compensate for temporal variations in one or more anatomic and/or physiologic features in the anatomic model.

2. The method according to claim 1, further comprising acts of acquiring a scout scan of the body volume and generating the reconstructed image.

3. The method according to claim 1, further comprising an act of retrieving a previously stored reconstructed image of the body volume 4. The method according to claim 1, further comprising an act of presenting the adjusted acquisition protocol to an operator for approval and/or further adjustment.

5. The method according to claim 1 further comprising an act of further adjusting the adjusted acquisition protocol during imaging based on feedback from analysis of previously acquired images.

6. The method according to claim 5, further comprising an act of storing the acquired images in a repository for later retrieval as initially provided reconstructed image for fitting of the anatomical model.

7. A non transitory computer readable medium including a computer program product which when executed on a computer performs a method for dynamic medical imaging of a body volume, the method comprising acts of:
   providing a reconstructed image of the body volume, an anatomic model of the body volume, and a dynamic model for temporal variations in one or more features in the anatomic model;
   fitting the anatomical model to the body volume to the reconstructed image of the body volume;
   imaging the body volume using an acquisition protocol initially comprising a preliminary acquisition protocol; and
   during the imaging,
      adjusting the acquisition protocol to compensate for temporal variations in one or more anatomic and/or physiologic features in the anatomic model.

8. A non-transitory computer program product which when executed on a computer performs a method of updating a medical imaging apparatus, the method comprising acts of:
   adjusting a preliminary acquisition protocol for dynamic medical imaging of a body volume;
   installing software applications that are based on data representing dynamic model for temporal variations in one or more feature, in an anatomic model;
   imaging the body volume using an acquisition protocol initially comprising a preliminary acquisition protocol; and
   during the imaging,
      adjusting the acquisition protocol to compensate for the temporal variations in said one or more anatomical and/or physiologic features in the anatomic model.

9. A medical imaging apparatus comprising:
   a unit configured to
      perform a scout scan of a body volume to be used to form a reconstructed image of the body volume;
      retrieve an anatomic model of the body volume and a dynamic model for temporal variations in one or more feature in the anatomic model; and
   a processor configured to
      fit the anatomic model of the body volume to the reconstructed image,
      image the body volume using an acquisition protocol initially comprising a preliminary acquisition protocol; and
      during the imaging
         adjust the acquisition protocol to compensate for the temporal variations in said one or more features.

10. The apparatus according to claim 9, further comprising a repository for holding acquisition protocols and means for retrieving the preliminary acquisition protocol from the repository and for storing an adjusted acquisition protocol for a patient in the repository.

* * * * *